United States Patent
Wang et al.

(10) Patent No.: US 7,311,930 B2
(45) Date of Patent: Dec. 25, 2007

(54) HERBAL COMPOSITION FOR TREATMENT OF CHRONIC RENAL FAILURE AND METHOD TO PRODUCE THEREOF

(75) Inventors: Gang Wang, Jiangsu (CN); Wei Xiao, Jiangsu (CN)

(73) Assignee: Jiangsu Kanion Pharmaceutical Co., Ltd., Jiangsu (CN)

( * ) Notice: Subject to any disclaimer, the term of this patent is extended or adjusted under 35 U.S.C. 154(b) by 202 days.

(21) Appl. No.: 10/486,405

(22) PCT Filed: Jul. 23, 2002

(86) PCT No.: PCT/CN02/00512

§ 371 (c)(1),
(2), (4) Date: Feb. 5, 2004

(87) PCT Pub. No.: WO03/013560

PCT Pub. Date: Feb. 20, 2003

(65) Prior Publication Data

US 2004/0265397 A1     Dec. 30, 2004

(30) Foreign Application Priority Data

Aug. 6, 2001  (CN) .............................. 01 1 27084

(51) Int. Cl.
*A61K 36/43*   (2006.01)
*A61K 36/284*  (2006.01)
*A61K 36/815*  (2006.01)

(52) U.S. Cl. ..................... 424/773; 424/776; 424/777; 424/738

(58) Field of Classification Search ................. None
See application file for complete search history.

(56) References Cited

U.S. PATENT DOCUMENTS 4,813,613 A * 3/1989 Salete .................. 241/7

FOREIGN PATENT DOCUMENTS

| CN | 93107772.9 | 1/1995 |
| CN | 95119862.9 | 6/1998 |
| CN | 98122139.4 | 6/2000 |

OTHER PUBLICATIONS

English abstract of CN 1066603 (1992).*
English abstract of CN 1097272 (1995).*
English abstract of CN 1104118 (1995).*
English abstract of CN 1259363 (2000).*
English abstract of CN 1056535 (2000).*
English abstract of CN 1057011 (2000).*
English abstract of CN 1059921 (2000).*

* cited by examiner

*Primary Examiner*—Susan Coe Hoffman
(74) *Attorney, Agent, or Firm*—Harness, Dickey, & Pierce, P.L.C.

(57) ABSTRACT

The invention discloses a medicine that can treat CRF and the preparation method of it, which mainly make up of fleece-flower root, dodder, pseudostellaria root, atractylodes rhizome, wolfberry fruit, *Achyranthes* root the invented medicine absorb quickly, have good curative effect, with high content of effective component and admit is convenience.

14 Claims, No Drawings

HERBAL COMPOSITION FOR TREATMENT OF CHRONIC RENAL FAILURE AND METHOD TO PRODUCE THEREOF

TECHNIQUE FIELD

This invention relates to a kind of medicine and its preparation, which is used to treat CRF.

BACKGROUND TECHNIQUE

CRF (chronic renal failure) is many primary and secondary nephropathys' end pathologic stage, which is caused by the nephron's necrobiosis and charactered by the kidney related abnormity of the excretory function, instability of the internal environment and endocrine disorder. It is a serous and refractory disease in the clinic and is one of the common diseases which affect the human's health and cause people to die. According to the statistic data of north America, west European and Australia, about 100~50 persons one year in a million people develop to the stage of renal failure, what's more the number of the people who have developed to the stage of uremia is on a upward trend. The recent investigation in the America shows that in the past 10 yeas, the annul growth rate of the nephropathy patients in the final stage is reaching 9%, the incidence of the disease is beyond 200 person every one million, and this investigation forecasted that the total number of the uremia patients would exceed 250000 person. The related epidemiologic data of China indicated that the death rate of the CRF is 67.6 people every one million, and it is 10% of the total death rate. Though the dialysis and the renal transplantation are both the effective method, they can't prevent and cure the disease in the early and middle stage. What's more the expensive cost is a heavy duty to both the country and the family. In the world, there are only about 20% area owning the instrument of dialysis, and in China no more than 1.0% of the final-stage-nephropathy patients can receive the therapy of dialysis, and even less people have the chance to do the renal transplantation. According to this reality, it is a focus to study the non-dialysis therapy and medicine of the CRF in the field of the nephropathy therapeutired peony root.

In the recently years, the researcher of the whole world have finished a lot of studies on the mechanism of the rest nephron's necrobiosis. In the field of the non-dialysis therapy, they developed some medicines with clearly chemical structure and simple components, such as Ketosteril (some essential amino acid and keto acid), ACEI, active Vit D, EPO and etc. But all these medicines are hard to be widely used in China, because they are expensive and can only release some of the symptoms. ACEI can inhibit the remaining nephrons's fibrosis, but the individual variation is very big and there are many side-effection. The Chinese materia medica preparation "Mao shen kang pian" which reported effective to treat CRF in Chinese journals is individual component. Rhubarb is the principal drug in the "niao du qing chong ji", and this Chinese patent medicine's main effect is eliminating the evil factors. The inventor believes that the mechanism of the CRF is the declination of "the primordial qi of the kidney" and the stasis of the mucous toxin. The declination of the "primordial qi of the kidney" means the declination of kidney-qi, kidney-yin and kidney-yang; the stasis of mucous toxin means that the metabolism waste produced by the body can't be discharged because of the declination of "the primordial qi of the kidney". The declination of "the primordial qi of the kidney" is the principal reason the CRF, while the stasis of the mucous toxin is the main manifestation of the disease. Because of this mechanism, this disease's excessive manifestation is caused by the deficiency of the organs, and the deficiency-in-origin-and-excess-in-superficiality syndrome is usual seen. But by so far, there is not a drug that can protect the primordial of the kidney, balance the kidney-yin and kidney-yang, reinforce and reduce normally, strengthen the body resistance and discharge the mucous evil at the same time.

In a word, CRF is a serious and refractory clinical disease. Its incidence is on an upward trend and the related mortality has reached 10% of the total people's death rate. Because the cost of the dialysis and the transplantation is expensive while the kidney is difficult to get and the transplantation has so many complicating syndrome, dialysis and transplantation is difficult to be popularized. So that, developing the effective Chinese patent medicine on treating CRF is a worthy direction to be studied.

Technology Content

The purpose of this invention is to provide a medicine which can treat CRF and its preparation.

The purpose of this invention comes to the reality by the technical proposal as following:

The basic materials of the invented medicine are that:

| | |
|---|---|
| Fleece-flower root | 100-600 part-by-weight |
| dodder | 100-600 part-by-weight |
| Pseudostellaria root | 100-600 part-by-weight |
| atractylodes rhizome | 100-600 part-by-weight |
| Wolfberry fruit | 100-600 part-by-weight |
| Achyranthes root | 100-600 part-by-weight |

The following herbs can be added into the basic materials:

| | |
|---|---|
| Lycopus herb | 100-600 part-by-weight |
| red peony root | 100-600 part-by-weight |
| Indian bread | 100-600 part-by-weight |
| alisma rhizome | 100-600 part-by-weight |
| Psyllium seed | 100-600 part-by-weight |
| rhubarb | 100-600 part-by-weight |

The invented medicine can be prepared as following:

Take the prepared fleece flower root and the prepared rhubarb then crush them in to raw flour. According to the percolation recorded in the entry about fluidextract and extract, use 60%-90% alcohol as the dissolvent, soakage the raw flour then do the percolation, collect the percolate then retrieve the alcohol, condense to get the fluidextract; take atractylodes rhizome and crush it into raw flour, put the raw flour into the water 2-8 times of it for 2-8 hours, then distill the mixture to get the volatile oil from the vapor, keep the gruffs and the solution alone; dissolve the volatile oil into 60-90% alcohol then on the method of colloid mill grind the mixture to package the volatile oil. The ratio of volatile oil solution to β-dextrin is 1:4-10 and the ratio of β-dextrin and water is 1:1-3. After the grind, the mash is made, dehydrate the mash then crush it into powder. The powder is the volatile oil's clathrate; Cook the wolfberry fruit and indian bread in the water for 1-3 times and every time is 1-3 hours, the amount of the water is 6-10 times weight of the two herbs. Combine all the cooked water together then concentrate it, do the centrifugation to get the centrifugate; put the atractylodes rhizome's gruffs, solution and the rest of the herbs together, cook the mixture in the water for 1-3 times, each time is 1-2 hours and the water is 6-10 times weight of the mixture. Mingle all the cooked water and filtrate it. Concentrate the filtrated water then cool it down to the room temperature. Add alcohol to this solution until the alcohol's concentration up to 50-70%, standing the mixture to get the supernate solution. Retrieve the alcohol from the supernate solution and put the rest of it with the fluid extract (rhubarb, fleece-flower root) and the centrifuged extract (wolfberry fruit and fl), concentrate the mixture and dehydrate it in a low pressure, then crush the dry extract into fine powder. Mingle the fine powder, the volatile oil clathrate and the adjuvant together. The mixture can be made into many dosage forms needed in the clinic.

The fleece-flower root mentioned above can be exchanged by the prepared fleece-flower root. The atractylodes rhizome mentioned above can be exchanged by prepared atractylodes rhizome and the rhubarb can be exchanged by prepared rhubarb.

The identification method for quality control of the invented medicine (take the tablet for example) is that: crush 5 tablets into fine powder then dissolve the powder in the 30 ml chloroform and extract in the circumfluence for 1 hour. Filtrate the mixture. Distil the residue to dryness then dissolve it in 40 ml alcohol. Extract the solution in circumfluence for 1 hour, filtrate the solution and distil the filtrate to dryness. The residue dissolved to 1 ml in the alcohol is served as the solution for test. 1 g fleece-flower root is made into the control solution on the same way. Test the solutions by the thin layer chromatography. Imbibe 5 μl of the two kinds solutions and drop the solutions on the same silica gel G thin layer separately. Use aceticether-methanol-water (100:17:13) mixture as the developing agent and expand the two points at the stretch of 10 cm. Take the thin layer out and dry it in the air. Check the dehydrated lay under the 365 nm ultraviolet light and there should be the same fluorescent spot in the test chromatogram at same place of the control chromatogram; Take 4 piece of tablets and crush them into fine powder, then add 30 ml alcohol to the powder and distil the mixture in the circumfluence for 30 minutes. Filtrate the mixture to get the filtrated liquid and add 2 ml muriatic acid. After 1 hour abstraction in the circumfluence, concentrate the solution to 2 ml, then add 5 ml water and extract the new solution in 15 ml chloroform for 2 times. Distil the 30 ml chloroform to dry then get the dried extract. Add chloroform to solute the extract to 2 ml then get the test solution. Dissolve oleanolic acid into the methanol at the concentration of 1 mg/ml to get the control solution. According to the method of thin layer chromatography, imbibe the two solutions each 5 μl then drop them to the same silica gel G thin layer separately. Using chloroform-acetone (1:1) as the developing agent, expand the two points then take out the thin layer to dry in the air. Spray the 10% vitriolic-acid-alcohol solution to the thin layer, and then blow the thin layer with the hot air until the two points become clear. There should be the same color spot in the test solution's chromatogram at the same place of the control chromatogram; Dissolve 5 tablets in 30 ml methanol and extract in the circumfluent for 30 minutes. Filtrate the mixture and distil the filtrated liquid to dry. Collect the residue then dissolve it in 15 ml water. Extract the solution in the saturated n-butyl alcohol for 2 times on the condition of jerking. Each time the n-butyl alcohol is 15 ml. Mingle the two pieces of extracted liquid then distil the mixed liquid to dry. Dissolve the obtained residue in methanol to 1 ml to get the test solution. Prepare the paeoniflorin-methanol solution at the concentration of 1 mg/ml as the control solution. According to the method of thin layer chromatography, imbibe the two solutions each 5 μl then drop them to the same silica gel G thin layer separately. Using chloroform-ethylacetate-methanol-methanoic acid (40:5:10:0.2) as the developing agent, expand the two points then take out the thin layer to dry in the air. Spray the 10% vitriolic-acid-alcohol solution to the thin layer, and then blow the thin layer with the hot air until the two points become clear. There should be the same color spot in the test solution's chromatogram at the same place of the control chromatogram.

The content test method for quality control of the invented medicine is that: remove 10 tablets' clothing sheet, then weight them with accuracy. Crush these tablets to fine powder and weight out 1 g of the powder accurately. Put the powder into a 250 ml roundbottomed flask, then add 25 ml 2.5 mol/L sulfuric acid and 40 ml chloroform. After 4 hours of circumfluence, separate the chloroform layer. Add 40 ml chloroform to the rest solution and extract in the condition of circumfluence and waterbath for another 3 hours. Separate the chloroform layer and extract the rest solution with 10 ml chloroform for 3 times. Combinate all the chloroform then water-wash it to neutrality. Retrieve the chloroform and dissolve the residue into the methanol. Adjust this solution to 5 ml accurately to serve as the test solution. Prepare the emodin-methanol solution at the concentration of 0.1 mg/ml as the control solution. According to the method of thin layer chromatography (China pharmacopoeia version 1995 the No. 1 part supplement VIB), imbibe the test solutions 5 μl, the control solution 2 μl and 8 μl, then drop them to the same silica gel G thin layer separately. Using benzene-ethyl acetate-methanol-methanoic acid-water (3:1:0.2:0.05:0.5) as the developing agent, expand the 3 points at the stretch of 10 cm, then take out the thin layer to dry in the air. According to scan method of the thin layer chromatography (China pharmacopoeia version 1995 the No. 1 part supplement VIB), scan the chromatography at the wavelength: $\lambda_S$=435 nm, $\lambda_R$=600 nm. Measure and calculate the absorbance quantity of the test solution, then contrast it with the control solution and calculate to get the content of the test solution.

Each tablet must own no less than 0.07 mg emodin. Oral administration, 4 pieces of tablets one time, 3 times a day.

EXPERIMENT EXAMPLE 1

The Invented Medicine's Clinical Curative Effect Research in the CRF Patients

The Clinical Research: the invented medicine was used to treat 52 CRF patients. The other 16 matched patients were treated by "shenkangning". By the comparison, the invented medicine was appraised about the clinical effect, the security and the side effect.

1 The Data and the Method 1.1 Patient and the General Data

The age was between 18 to 79 years old, and the average level was 42.4±17.8 years old. The number of the man was 32, while the number of the woman was 36. The rate of man to woman was 1:1.12. The total number of the patients was 68; the treatment group had 52 patients while the control group had 16 patients.

There was no significant difference about the gender structure between the two groups (P>0.1). (see table 1)

There was significant difference about the age structure between the two groups (P>0.01). There were more old patients in the treatment group. (see table 2)

There was no significant difference about the course of the disease between the two groups (P>0.1). (see table 1)

There was no significant difference about the symptom score between the two groups (P>0.01). (see table 1)

There was significant difference about the disease stage between the two groups (P<0.01). The constituent ratio of the patients who were on the stage of azotemia or uremia is higher in the treatment group; than that in the control group. (see table 3)

1.2 The Diagnostic Criteria 1.2.1 The Diagnostic Criteria of the Modern Medicine:

(1) The patient had the history of chronic renal disease.

(2) There were CRF related clinical symptom and metabolic disorder.

(3) The concentration of the serum creatinine (Scr) was beyond 133 μmol/L. The CRF can be divided into 3 stages, the criteria is as following.

Stage 1 (the compensatory phase of the renal incompetence): the GFR 50-80 ml/minute; Scr 133-177 μmol/L.

Stage 2 (the decompensatory phase of the renal incompetence): the GFR 20-50 ml/minute; Scr 178-442 μmol/L.

Stage 3 (the renal failure phase): the GFR 10-20 ml/minute; Scr 443-707 μmol/L.

Stage 4 (the uremia phase): the GFR <10 ml/minute; Scr 707 μmol/L.

TABLE 1 the comparison on the gender, disease course, symptom score between the two groups

| Group | Case number | Gender structure Man | Gender structure Woman | Disease course(month) | Symptom score |
|---|---|---|---|---|---|
| Treatment group | 52 | 24 | 28 | 19.88 ± 27.26 | 45.43 ± 10.94 |
| Control group | 16 | 8 | 8 | 18.69 ± 11.64 | 42.88 ± 4.5 |

There was no difference between the two groups about the gender structure, the disease course and the symptom score (P>0.1), so that the two group were comparable at these sides.

TABLE 2 the comparison on the age construction between the two groups

| Group | Case number | 18-30 years (%) | 31-60 years (%) | 61-80 years (%) |
|---|---|---|---|---|
| Treatment group | 52 | 8(15.3) | 25(48.1)* | 21(41.2)* |
| Control group | 16 | 3(18.3) | 11(68.8)* | 2(3.8)* |

There was significant difference between the 2 groups on the age structure (X2 test, * p<0.01). The patients of 31-60 years old had a remarkable higher ratio in the control group than in the treatment group, while in the treatment group the patients of 61-80 years old had a bigger ratio that in the control group.

TABLE 3 the comparison of the disease stage in the two groups

| Group | Case number | Compensatory phase (%) | Azotemia (%) | Uremia (%) |
|---|---|---|---|---|
| Treatment group | 52 | 7(13.46) | 24(46.15) | 21(40.38) |
| Control group | 16 | 10(62.5) | 5(31.25)* | 1(6.25) |

There was significant difference between the 2 groups on the disease stage (X2 test, P<0.01). In the treatment group, the patients who had reached the stage of azotemia or uremia had a higher ratio than that in the control group, while the patients who were still at compensatory phase had a higher ratio than the treatment group. The difference was remarkable (P<0.01)

1.2.2 The Criteria to Differentiate the Syndromes in TCM.

The criteria referred to the symptom—"deficiency of both qi and yin with internal accumulation of damp turbidity" in the "TCM criteria for the differentiation of syndromes in CRF", which was approved in the Chinese national TCM academy's third nephropathy academic conference of TCM, and "the clinical research criteria of the new Chinese drug to treat the uremia".

The Symptom of "the Spleen and Kidney's Deficiency of Both qi and yin":

The patient's face seems short of luster; he feels short of energy and easy to be tired; it is lassitude at the waist and knee; the skin is dry; he feels dry in the mouth and lip, but doesn't want drink much water; he may feel hot in the palm of the hands and the underside of the foot; the stool may be dry or watery; the urine's quantity reduces and its color turns yellow, while somebody has great deal of tint color urine especially at night; the patient's tongue is pale and with indented margin; the pulse is deep and thready.

The Symptom of "the Internal Accumulation of Damp Turbidity":

The patient has the symptom as following: nausea and vomit, anorexia and abdominal distention, heaviness sensation in the limbs and sleepy, thick and greasy fur.

1.3 The Selection Criteria 1.3.1 The patient has been diagnosed as the CRF according to the criteria.

1.3.2 The patient accepts the entire necessary tests voluntarily, which are needed to estimate the curative effect.

1.3.3 The patient's age is between 18 to 79 years old and he must have a history of chronic renal disease and have reached the renal incompetence phase.

1.4 The Exclusion Criteria

If the patient has any conditions as following, he is not allowed to take part in this research.

1.4.1 The patient has received peritoneal dialysis or hemodialysis.

1.4.2 The patient is in the period of pregnancy or lactation.

1.4.3 The patient is suffering from other serious diseases such as the angiocardiopathy, the hepatopathy and the hematopathy etc.

1.4.4 The patient can't administrate on the research's require so that the curative effect can't be estimated. Or the patient doesn't have the integrated material so that the security and the curative effect can't be estimated.

1.5 The Elimination Criteria 1.5.1 The patient has to stop the treatment because of the unexpected reasons but the untoward reactions.

1.5.2 The patient has to stop the treatment because of the untoward reactions. This kind of cases must be calculated separately and be studied to look for the reasons.

1.6 The Research Method 1.6.1 Grouping, Administration and the Course of the Treatment There are 52 patients in the treatment group. They were treated by the invented medicine made from prepared fleece-flower root, dodder pseudostellaria root, *Achyranthes* root, atractylodes rhizome, wolfberry fruit, etc (supplied by Lianyun'gang kangyuan Pharmaceutical Co Ltd. Batch number 9808127) on the administration of 4 pieces of tablet one time, 3 times a day, per os. 2 months was one course of treating. There were 16 patients in the control group and the matching medicine was "shenkangning pian" which was made from astragalus root, aconite root, qinseng, indian bread, alisma rhizome, chinese yam, leonurus heterophyllus etc. The effect of "shenkangning pian" is "nourishing qi and warming the kidney; activating the blood and excreting the dampness". It can be used to treat the chronic nephritis, chronic renal incompetence. (produced by Hangzhou zhengda qingchunbao Pharmaceutical Co Ltd. The Ministry of Health medicine criteria 1992 WS-B-1153-92) The administration was 5 pieces of tablet one time and 3 times a day, per os. 2 month was one course of treating.

The two kinds of medicines both have the effect of supporting healthy energy and eliminating evils. Because their effects and indications are similar, the two medicines are comparable.

1.6.2 The Main Indexes (1) Observe the symptoms of "deficiency of both qi and yin with internal accumulation of damp turbidity" and evaluate 6,4,2,0 according to the severity: severeness, moderate, gentleness and none. Record the symptom score once a week.

(2) Observation about the untoward reaction: observe and record the untoward reaction.

(3) The Major Test Indexes:

The indexes related to the curative effect: BUN, Scr, Ua, CO2-CP, the blood electrolyte test, the blood pressure, 24 h Upro, the routine urine examination, Ucr, the osmotic pressure of the blood and urine, the B-type ultrasonic examination about the kidneys.

The indexes related to the security: the usual checkup; the routine test of the blood, urine and stool; the hepatic and renal function examination; ECG, the thoracic X-ray test.

1.6.3 The Criteria of the Effectiveness (1) Remarkably effective: i) the symptoms remarkably relieve or disappear; ii) the endogenous creatinine clearance ratio increases $\geq 30\%$; iii) the Scr decreases $\geq 30\%$ or to the normal range.

On the basis of i), if realized any target of ii) or iii), the treatment can be judged to be remarkably effective.

(2) Effective: i) the symptoms relieve or disappear; ii) the endogenous creatinine clearance ratio increases $\geq 20\%$; iii) the Scr decreases $\geq 20\%$ iv) If analysis the Scr value's reciprocal or logarithm before and after the treating by the method of linear regression equation, the slope is remarkably meaningful.

(3) Stable: i) the symptoms relieve; ii) the endogenous creatinine clearance ratio increases <20%; iii) the Scr decreases <20%; iv) If analysis the Scr value's reciprocal or logarithm before and after the treating by the method of linear regression equation, the slope is meaningful.

On the basis of i), if realized any target of ii), iii) or iv), the condition after the treating can be judged to be stable.

(4) Ineffective: if the patient's change can't reach any of the three standards mentioned before, the treatment is ineffective.

1.6.4 The Criteria of the Effectiveness about the TCM Symptom "Deficiency of Both qi and yin with Internal Accumulation of Damp Turbidity"

(1) Remarkably effective: the score of the TCM symptoms have reduced 75-100%.

(2) Effective: the score of the TCM symptoms have reduced 35-74%.

(3) Ineffective: the score of the TCM symptoms have reduced no more than 35%.

TABLE 4 the curative effective contrast of the two groups

| Group | Case number | Remarkable effective (%) | Effective (%) | Stable (%) | Ineffective (%) | Total effective rate (%) |
|---|---|---|---|---|---|---|
| Treatment group | 52 | 14 (26.9) | 27 (51.9) | 3 (5.7) | 8 (15.4) | 41 (78.8) |
| Control group | 16 | 1 (6.25) | 3 (18.75) | 4 (25) | 8 (40) | 4 (25) |

Note: The comparison of the curative effect between the 2 groups (Radit test): P<0.01

It can be seen from table 4 that: the total effective rate of the treatment group is 78% and this value is remarkably higher than that of the control group, of which the effective rate is 25%. The difference is significant (P<0.01)

2.2 The Major Test Indexes for Approving the Curative Effect (1) BUN and Scr, (See Table 5, 6)

TABLE 5 the contrast of BUN value between the two groups and its relation to the course ($\overline{X} \pm S$) mmol/L

| group | case number | Before administration | after administration 1 month | 2 monthes |
|---|---|---|---|---|
| Treatment group | 52 | 19.10 ± 10.44 | 18.30 ± 9.23 | 15.737 ± 8.85* |
| control group | 16 | 9.81 ± 2.49 | 9.27 ± 1.59 | 9.39 ± 2.06 | note:
The comparison of the BUN value before and after the treating (t test)
*P < 0.05;

Table 5 shows that the invented medicine can reduce the BUN significantly and the effect usually appears from the 2 months. The improvement was significant (P<0.05). It was supposed that the course of treatment be 2 months. There was no significant chance of the BUN before and after the treating in the control group (P>0.05).

TABLE 6 the contrast of Scr value between the two groups and its relation to the course ($\overline{X} \pm S$)μmol/L

| Group | case number | Before administration | after administration 1 month | 2 monthes |
|---|---|---|---|---|
| treatment group | 52 | 535.96 ± 374.58 | 487.76 ± 329.85 | 408.02 ± 303.32* |
| control group | 16 | 180.73 ± 60.27 | 189.91 ± 61.48 | 198.78 ± 74.35 |

Note:
The comparison of the Scr value before and after the treating (t test)
*P < 0.05

Table 6 shows that the invented medicine can reduce the Scr value one month after the treating. After two months of treatment the reduce of the Scr is significant (P<0.05). It was supposed that the course of treatment be 2 months. There was no significant change of the Scr before and after the treating in the control group (P>0.05) (P<0.05).

(2) $CO_2$-CP, Ua and K+ (See Table 7)

TABLE 7 the contrast of $CO_2$-cp, Ua and K+ between the two groups ($\overline{X} \pm S$)mmol/L

| group | Case number | $CO_2$-cp | | Ua | | K+ | |
| --- | --- | --- | --- | --- | --- | --- | --- |
| | | before administration | after administration | before administration | after administration | before administration | after administration |
| treatment group | 52 | 20.67 ± 4.79 | 22.0 ± 4.72 | 480.39 ± 169.78 | 468.77 ± 154.85 | 4.41 ± 0.73 | 4.36 ± 0.51 |
| control group | 16 | 23.01 ± 2.85 | 24.52 ± 3.34 | 323.43 ± 82.97 | 326.76 ± 99.78 | 4.46 ± 0.56 | 4.46 ± 0.67 |

Table 7 shows that there was no significant change of the CO2-cp, Ua and K+ before and after the treating (P>0.05)

(3) Rbc, Hb and ALB (See Table 8)

TABLE 8

The contrast of Rbc, Hb and ALB between the two groups ($\overline{X} \pm S$)

| group | case number | RBC($\times 10^{12}$/L) | | Hb(g/L) | | ALB(g/L) | |
| --- | --- | --- | --- | --- | --- | --- | --- |
| | | before administration | after administration | before administration | after administration | before administration | after administration |
| treatment group | 52 | 3.28 ± 1.09 | 3.33 ± 1.11 | 94.23 ± 33.42 | 94.95 ± 38.77 | 34.58 ± 8.64 | 34.84 ± 6.16 |
| control group | 16 | 3.88 ± 0.80 | 3.85 ± 0.75 | 121.88 ± 22.11 | 122.93 ± 20.91 | 34.09 ± 5.75 | 35.34 ± 5.51 |

Table 8 shows that there was no significant change of the Rbc, Hb and ALB before and after the treating (P>0.05)

(4) Ucr and 24 h Upro (See Table 9)

TABLE 9

The contrast of Ucr and 24 h Upro between the two groups ($\overline{X} \pm S$)

| group | case number | Ucr(μmol/L) | | 24 hUpro (g/d) | |
| --- | --- | --- | --- | --- | --- |
| | | before administration | after administration | before administration | after administration |
| Treatment group | 30 | 4349.09 ± 1734.85 | 5832.08 ± 1452.39** | 1.38 ± 0.57 | 1.27 ± 0.25 |
| control group | 16 | 4470.92 ± 1047.38 | 4504.71 ± 1258.69 | 1.33 ± 0.62 | 1.17 ± 0.63 |

Note:
The comparison of the Ucr and 24 h Upro before and after the treating in the same group (t test):
**p < 0.01

Table 9 shows that the invented medicine had improved the Usr significantly (P<0.01) in the treatment group, while there were no significant change before and after the treating in the control group (P>0.05). There were no significant change on the 24 h Upro before and after the treating in the both groups (P>0.05).

(5) The Osmotic Pressure of the Blood and Urine (See Table 10)

TABLE 10

The contrast of the osmotic pressure of the blood and urine between the two groups before and after treatment ($\bar{X} \pm S$)

| group | case number | osmotic pressure of the blood | | osmotic pressure of the urine | |
|---|---|---|---|---|---|
| | | before administration | after administration | before administration | after administration |
| treatment group | 30 | 286 ± 45.58 | 474 ± 137.52** | 321.06 ± 90.77 | 423.50 ± 95.87** |
| control group | 16 | 293 ± 52.58 | 344.20 ± 92.34* | 451.63 ± 187.96 | 462.25 ± 140.27 |

Note:
The comparison of the osmotic pressure of the blood and urine before and after the treating (t test):
*$P < 0.05$;
**$P < 0.01$ Table 10 shows that the invented medicine had improved the osmotic pressure of the blood and urine in the treatment group, and the change was significant ($P<0.01$); In the control group, the treatment had improved the osmotic pressure of the blood and urine too, and the change was significant ($P<0.05$).

(6) The Change of the Symptom Score

TABLE 11

The contrast of the symptom scores between the two groups before and after treatment ($\bar{X} \pm S$)

| group | case number | before administration | After administration |
|---|---|---|---|
| treatment group | 52 | 42.875 ± 4.52 | 23.02 ± 0.022**$^\Delta$ |
| control group | 16 | 41.025 ± 4.31 | 30.04 ± 1.68* |

Note:
The comparison of the symptom scores before and after the treating (t test):
*$P < 0.05$;
**$P < 0.01$;
The comparison of the symptom scores after the treating between the groups (t test):
$^\Delta P < 0.05$ Table 11 shows that both the two kind of medicines can meliorate the symptoms remarkably ($P<0.05$ and $P<0.01$), while the score of the treatment group was higher than that of the control group ($P<0.05$).

2.3 The Observation of the Security.

None of the patients had abnormal symptom or physical sign in the two groups, and the security indexes such as ECG, the hepatic function examination and the X-ray check didn't express any abnormal sign.

3. Discussion and the Clinical Research Result

The invented medicine had a total effective ratio of 78.8%, remarkably effective ratio 26.9% in treating the CRF. While the control medicine's total effective ratio was 25%, remarkably effective ratio was 6.25%. Both the total effective ratio and the remarkably effective ratio were higher than that of the control group, and the difference was significant by the statistired peony root analysis ($P<0.01$).

This invented medicine has a gentle function. Its characters are that: nourishing qi but not stagnating qi; nourish kidney but not stagnating; warming the yang but not causing dry; eliminating the evil but not hurting the vital qi; even reinforcing and reducing. So that this invented medicine can postpone the course of the CRF by the even treating. At the same time, because there are no untoward reactions such as: bellyache, diarrhea and inappetence etc, the invented medicine can be admitted for a long period safely. As mentioned before, the remarkably effective ratio of this medicine at the second month is 26.9%. The total effective ratio is 78.8% and the stable ratio is 5.7%, it is worth a further research.

EXPERIMENT EXAMPLE 2

(1) The Experimental Research of the Invented Medicine's Effect on the CRF Rat Caused by Adenine Intake 1. The Model Building The male SD rats were fed 1 week for the adaptability. Then the rats were fed 2% adenine by gastrogavage on the dose of 250 mg/kg/d once a day. Chose 10 rats of the same batch as the control group which were fed distilled water by gastrogavage on the dose of 250 mg/kg/d once a day. After 4 weeks of feeding, the rats fed adenine were weighted and collected blood from the orbital cavity. The BUN and Scr were measured to select the rats whose BUN were between 20.00~32.00 mmol and Cr were between 86.00~136.00 μmol/L. Based on the BUN and Scr level the total 60 rats selected were divided into 5 groups at random and receive the treatment.

2. The Group and the Dosage (1) The normal control group: 10 SD male rats were fed distilled water on 10 ml/kg once a day by gastrogavage.
(2) The model control group: 12 SD male rats were fed distilled water on 20 ml/kg once a day by gastrogavage.
(3) The treatment group with the invented medicine on the high dosage (H group for short): 12 SD male rats were fed the invented medicine on the dosage of 43.3 g/kg/d (42 times of the human's dosage) by gastrogavage twice a day. The concentration of the medicine suspending liquid was 10.8 g/ml.

(4) The treatment group with the invented medicine on the middle dosage (M group for short): 12 SD male rats were fed the invented medicine on the dosage of 21.65 g/kg/d (21 times of the human's dosage) by gastrogavage once a day. The concentration of the medicine suspending liquid was 10.8 g/ml.

(5) The treatment group with the invented medicine on the low dosage (L group for short): 12 SD male rats were fed the invented medicine on the dosage of 10.83 g/kg/d (10.5 times of the human's dosage) once a day by gastrogavage. The concentration of the medicine suspending liquid was 5.4 g/ml.

(6) The positive medicine control group (shenkangning group for short). 12 SD male rats were fed "shenkangning" on the dosage of 10.38 g/kg/d (22.4 times of the human's dosage) by gastrogavage once a day. The concentration of the medicine suspending liquid was 5.19 g/ml.

The dosages of the invented medicine used in the 3 groups were on the rate of 1:2:4.

3. The Course of the Treatment

The medicine was administrated for 6 weeks.

4. The Indexes (1) The body weights were measured every week before and after the treating.

(2) The bloods were collected from the orbital cavity before the treating, 3 weeks and 6 weeks after the treating. The BUN, SCr, TP, ALB and Hb etc were measured (3) The rats were killed when the treatment was over. The kidneys were observed with the eye and measured of the weight. The kidney index (the weight of one kidney mg/body weight g) was calculated;

(4) 4 rats were selected every group from the lightest to the heaviest to get the nephridial tissue. The tissues from the kidneys were dyed on the methods of HE, PAS and Masson then observed under the optical microscope.

(5) 2 pieces of sample kidneys were selected every group to make the ultrathin section. The sections were observed under the electronic microscope.

The histopathology inspection was undertaken by the PLA nephropathy research institute of Nanjing military district chief hospital.

(II) The Experimental Research of the Invented Medicine's Effect on the CRF Rat Caused by ⅚ Nephrectomy.

1. The model building

80 SD male rats were fed and observed for 1 week. 70 rats were selected to receive the ⅚ nephrectomy. The operation was divided into 2 steps. After anesthetized with 2% pentobarbital, the rats were disinfected of the skin. Expose the left kidney from the flank, and then strip the renal anadesma. Exsect the two poles of the left kidney quickly. The exsected part must reach the ⅔ of the left kidney. Remove the right kidney one week after the first operation. Protect the adrenals carefully and put gelfoam over the incisions. Perform the hemostasis by compression after the operation. All the operation was done by one person. Strengthen the idea of the aseptic manipulation. All the rats received the operation were injected penicillin for 4 days. The other 10 rats were set as the control group. 4 weeks after the last operation, all the rats were weighted and collected blood from the orbital cavity. After the BUN and Cr were measured, all the rats were divided into 5 groups on the level of the BUN and Cr.

2. The group and the dosage: same to (1) 2

3. The course of the treatment: 4 weeks after the last operation, the rats which were made to model successfully received the treatment for 6 weeks.

4. The indexes: same to (1) 4.

The histopathology inspection was undertaken by the pathology laboratory of Nanjing Medical University.

Result:

(I) The effect of the invented medicine on the CRE rat caused by adenine intake

1. The Body Weigh and the Generalized Condition

TABLE 12

The effect of the invented medicine on body weight of the CRF rat caused by adenine intake (g, $\overline{X} \pm S$)

| group | dose (g/k) | BW before the treating | BW after the treating | | |
|---|---|---|---|---|---|
| | | | 2 weeks | 4 weeks | 6 weeks |
| normal control group | — | 164.20 ± 10.91 | 230.00 ± 22.36 | 295.50 ± 12.12* | 373.50 ± 24.73** |
| model control group | — | 170.83 ± 10.62 | 194.44 ± 15.29 | 248.13 ± 7.04$^\Delta$ | 305.00 ± 17.73$^{\Delta\Delta}$ |
| H group | 43.30 | 169.58 ± 8.91 | 216.25 ± 13.51 | 274.17 ± 14.43 | 369.10 ± 41.50** |
| M grou[ | 21.65 | 166.67 ± 12.67 | 208.00 ± 12.95 | 266.50 ± 12.70 | 336.00 ± 24.36* |
| L group | 10.83 | 170.00 ± 11.48 | 207.50 ± 7.83 | 263.75 ± 8.82 | 322.08 ± 17.25$^\Delta$ |
| Shengkangning group | 10.38 | 170.83 ± 10.62 | 207.50 ± 2.63 | 259.44 ± 7.68 | 314.00 ± 41.35$^\Delta$ |

*Comparing with model control group: p < 0.05;
**Comparing with model control group: p < 0.01.
$^\Delta$Comparing with normal control group: p < 0.05;
$^{\Delta\Delta}$Comparing with normal control group: P < 0.01.

After fed of adenine, the rats' body weight increased slowly; some rats' body weight even decreased. The food-entake of the rats decreased and the rats' fur appeared less of luster. The rats were out of spirits. Their ears and tails looked pale. The symptoms were found in both the treatment group and the control group but in the treatment group the symptoms were less serious. The growth of the treatment group was faster than that of the model control group, especially in the H group. The growth of the body weight in the H group and the M group was remarkably higher than that of the model control group (P<0.01; P<0.05). The growth in the shenkangning group was slower than that of the group treated with the invented group.

During the experiment, 4 rats died in the shengkangning group, 4 rats died in the model control group, and 2 rats died in the M group. One of the rats in the M group died for the incidence during the gastrogavage, the other rats died were not found with any abnormal organs except the large white kidney.

2. The Kidney Weight

TABLE 13

The effect of the invented medicine on kidney index (one kidney's weight/body weight) of the CRF rat caused by adenine intake

| group | dose (g/k) | Rats number | Body weight (g, $\overline{X} \pm S$) | Kidney weight(one side) (g, $\overline{X} \pm S$) | Kidney index (mg/g, $\overline{X} \pm S$) |
|---|---|---|---|---|---|
| normal control group | — | 10 | 373.50 ± 24.73** | 1.08 ± 0.2 | 2.85 ± 0.41** |
| model control group | — | 8 | 305.00 ± 17.73$^{\Delta\Delta}$ | 4.60 ± 1.08$^{\Delta\Delta}$ | 15.22 ± 4.22$^{\Delta\Delta}$ |
| H group | 43.30 | 12 | 369.10 ± 41.50** | 4.53 ± 0.77$^{\Delta\Delta}$ | 12.26 ± 1.60*$^{\Delta\Delta}$ |
| M group | 21.65 | 10 | 336.00 ± 24.36* | 4.32 ± 0.28$^{\Delta\Delta}$ | 12.94 ± 1.54$^{\Delta\Delta}$ |
| L group | 10.83 | 12 | 322.08 ± 17.25$^{\Delta}$ | 4.48 ± 0.56$^{\Delta\Delta}$ | 14.08 ± 2.17$^{\Delta\Delta}$ |
| Shenkangning group | 10.38 | 8 | 314.00 ± 41.35$^{\Delta}$ | 4.11 ± 0.46$^{\Delta\Delta}$ | 13.38 ± 2.46$^{\Delta\Delta}$ |

*Comparing with the model control group P < 0.05;
**Comparing with model control group P < 0.01;
$^{\Delta}$Comparing with the normal control group P < 0.05;
$^{\Delta\Delta}$comparing with the normal control group P < 0.01

The kidney weight of the rats fed with adenine increased remarkably (comparing with the normal control group P<0.01). The kidney index of the treatment group was smaller than the model group, especially that of the H group (P<0.05), but still larger than the normal group.

3. BUN and Scr

TABLE 14

The effect of the invented medicine on BUN of the CRF rat caused by adenine intake

| group | Dose (g/kg) | Before the treating | 3 weeks | 6 weeks |
|---|---|---|---|---|
| | | BUN(mmol/L, $\overline{X} \pm S$) | | |
| Normal control group | — | 9.97 ± 0.77**$^{\Delta\Delta}$ (10) | 8.50 ± 1.14**$^{\Delta\Delta}$ (10) | 8.16 ± 1.44**$^{\Delta\Delta}$ (10) |
| Model control group | — | 28.24 ± 5.57 (12) | 24.46 ± 2.41 (9) | 19.41 ± 2.61 (8) |
| H group | 43.30 | 28.63 ± 5.93 (12) | 19.41 ± 2.88* (12) | 9.02 ± 1.17**$^{\Delta\Delta}$ (12) |
| M group | 21.65 | 28.95 ± 5.17 (12) | 19.95 ± 2.76* (10) | 11.45 ± 2.13**$^{\Delta\Delta}$ (10) |
| L group | 10.83 | 27.68 ± 7.11 (12) | 19.71 ± 1.92* (12) | 15.52 ± 3.47*$^{\Delta}$ (12) |
| Shenkangning group | 10.38 | 26.61 ± 6.02 (12) | 24.48 ± 3.55 (9) | 20.15 ± 5.31 (8) |

*Comparing with the model control group p < 0.05,
**comparing with the model control group p < 0.01;
$^{\Delta}$Comparing with the shenkangning group p < 0.05,
$^{\Delta\Delta}$Comparing with the shenkangning group P < 0.01.

TABLE 15

The effect of the invented medicine on Scr of the CRF rat caused by adenine intake

| Group | dose (g/kg body weight) | Cr(mmol/L, $\overline{X} \pm S$) | | |
|---|---|---|---|---|
| | | Before the treating | 3 weeks | 6 weeks |
| normal control group | — | 72.57 ± 6.73ΔΔ (10) | 69.80 ± 5.56ΔΔ (10) | 70.79 ± 3.40**ΔΔ (10) |
| model control group | — | 91.45 ± 23.66 (12) | 98.88 ± 7.64 (9) | 103.95 ± 18.08 (8) |
| H group | 43.30 | 88.59 ± 30.26 (12) | 83.63 ± 10.42* (12) | 70.02 ± 20.69**ΔΔ (12) |
| M group | 21.65 | 87.88 ± 27.55 (12) | 85.65 ± 6.89* (10) | 64.65 ± 8.08**ΔΔ (10) |
| L group | 10.83 | 94.28 ± 38.28 (12) | 78.34 ± 9.65* (12) | 51.18 ± 14.43**Δ (12) |
| Shenkangning group | 10.38 | 94.92 ± 29.71 (12) | 94.08 ± 6.13 (9) | 92.93 ± 22.08* (8) |

*Comparing with the model control group, P < 0.05;
**Comparing with the model control group, P < 0.01;
ΔComparing with the shenkangning group P < 0.05;
ΔΔComparing with the shenkangning group P < 0.01.

Table 14 and table 15 shows that according to the increasing of the BUN, Scr, the model rats had reached the stage of CRF, after being fed adenine for 4 weeks. Treated for 6 weeks, the BUN and Scr of the treatment group were lower than that of the model group and shenkangning group. The difference was significant (P<0.01). The result indicates that this invented medicine can improve the renal function of the CRF rat.

4, Hb, TP and ALB with model control group and the shengkangning group, the difference was significant (P<0.01). The result indicates the invented medicine can improve the Rb of the CRF rat.

5. The Pathology Change (1) The General Pathology Change a. The Gross Change of the Kidney The kidney of the model group looks greenish yellow, cloudy swelling.

TABLE 16

The effect of the invented medicine on Hb, TP and ALB of the CRF rat caused by adenine intake

| group | Dose (g/kg) | Hb(g/L, $\overline{X} \pm S$) | | TP(g/L, $\overline{X} \pm S$) | | ALB(g/L, $\overline{X} \pm S$) | |
|---|---|---|---|---|---|---|---|
| | | Before the treating | After the treating | Before the treating | After the treating | Before the treating | After the treating |
| normal control group | — | 164.60 ± 5.40ΔΔ (10) | 165.00 ± 5.40ΔΔ (10) | 79.09 ± 3.61ΔΔ (10) | 74.60 ± 5.70ΔΔ (10) | 57.12 ± 2.99ΔΔ (10) | 54.53 ± 4.72ΔΔ (10) |
| model control group | — | 131.85 ± 8.35 (12) | 124.88 ± 7.32 (8) | 56.63 ± 12.58 (12) | 42.63 ± 3.54**ΔΔ (8) | 34.72 ± 5.87 (12) | 31.10 ± 4.85 (8) |
| H group | 43.30 | 142.91 ± 9.54 (12) | 170.25 ± 9.58ΔΔ (12) | 66.12 ± 14.65 (12) | 57.25 ± 3.55ΔΔ (12) | 37.73 ± 8.42 (12) | 38.69 ± 2.09* (12) |
| M group | 21.65 | 136.62 ± 6.32 (12) | 168.60 ± 13.29ΔΔ (10) | 58.94 ± 10.94 (12) | 55.65 ± 4.23ΔΔ (10) | 34.21 ± 6.73 (12) | 37.71 ± 2.67* (10) |
| L group | 10.83 | 138.78 ± 7.22 (12) | 157.08 ± 6.56**ΔΔ (12) | 55.80 ± 11.40 (12) | 49.83 ± 5.56 (12) | 34.25 ± 7.34 (12) | 35.73 ± 4.37* (12) |
| Shengkangning group | 10.38 | 137.24 ± 8.68 (12) | 135.13 ± 19.52 (8) | 56.94 ± 9.18 (12) | 45.54 ± 6.82 (8) | 34.62 ± 7.24 (12) | 33.93 ± 4.77 (8) |

*Comparing with the model control group, P < 0.05,
**Comparing with the model control group P < 0.01,
ΔΔComparing with the shenkangning group, P < 0.01

Table 16 shows that the Hb and the serum protein content were lower after the model building than that of the normal control group. After 6 weeks of treating with the invented medicine, the Hb was improved remarkably. Comparing The surface is smooth and granular. The section looks greenish yellow too.

There are many nonuniform microvoids in the section. The cortex is a little thick and the color is pale. The border of the cortex and the medulla is not clear. The kidneys of the treatment group are smaller than the model group. The kidney color of the treatment group is tawny.

b. The Microscopical Change of the Kidney Under the Optical Microscope

The Normal Control Group:

The renal glomerule capillary loops are open. There are no proliferation of the mesangial cell and matrix. No necrosis and fibrosis was found in the renal tubules and the renal mesenchyme. The interstitial cells distributes uniformly. The renal glomerule, tubules and the interstitial cells seem normal.

The Model Control Group: The renal glomerule capillary loops are not fully open. The renal capsules are thicker than usual. The fibrosis out of the renal capsule is obvious. Serious degeneration can be found among the renal tubules and mesenchyme. Most of the epithelial cells are flat. Little of the renal tubules are regenerating. Some of the tubules are lack of the membrane and dilate as bursiform. There are cellular cast in the enlarged tubules and some places have calcified. The mesenchyme has broadened with seriously fibrosis. The cells infiltrate in the mesenchyme diffusely. The walls of the arteries are thicker than usual.

H Group: The degeneration among the tubules is lighter than the control group. There are a little of proteic casts and vacuolar degeneration of the tubules at the border of the cortex-medulla. The interstitial fibrosis and the cellular infiltration are light. Few of foam cells disperse. There is no significant change of the renal glomerulus. In short, the pathological change is light than the model control group and the shengkangning group.

M Group: The renal glomerule's capillary loops open well. There is no proliferation of the renal mesentery. Very few epithelial cells on the parietal layer have proliferated. The pathological change in the renal tubules and matrix is light. Though there are interstitial fibrosis and cellular filtration, the pathological change is remarkable lighter than the model control group and the shengkangning group.

L Group: There is segmental proliferation of the renal mesentery in few of the renal glomenrules. Some of the glomerular capsules have thickened with the fibrosis out of the capsule. The epithelial cells of the renal tubule are flat. Some of the tubules are lack of the epithelial cells. Some of the tubules are filled with cellular cast. The matrix has broadened with the fibrosis and light cellular filtration. The pathological change is remarkably lighter than the control group and the shengkangning group.

Shengkangning Group: There is segmental proliferation of the renal mesentery in the renal glomenrules. Many renal glomenrular capsules have thickened with remarkable fibrosis out of the capsules. There is middle to heavy level interstitial fibrosis and there are many cells filtrating in the tissue. The matrix has broadened. The pathological change of the renal tubules and the matrix is serious. The epithelial cells of the renal tubule are flat. Few of the renal tubules are filled with cellular cast. The wall of the artery has thickened.

(2) The Change of the Kidney's Ultrastructure

Normal Control Group: The capillary vessel of glomerule is open, there is a few of red blood cells in the blood vessel and the vessel wall is lining with fenestra type endothelial cell, without swelling and hyperplasia. The basement membrane is even and without deposition of the compact complex. The thickness of the basement membrane is 110-60 nm (normal). The epithelial cells are also without swelling and vacuolar degeneration, whose foot processes are sharp. The mesentery is without enlargement. No cell hyperplasia, groundsubstance multiply or compact complex deposition is found. The epithelial cells of the renal tubule are of no obvious change and belong to the normal nephridial tissue.

Model Control Group: The epithelial cells of the renal tubule are swelling and there are lots of lysosomes in the cytoplasm. There are also many crystal like small bodies in the tubules and plenty of crystals in the epithelial cells and mesenchyme. The mesenchyme was infiltrated by lymphocytes. The fibrous cells and collagen fibril have proliferated obviously. Few basementmembrane of the renal tubule is thinner than normal or even ruptured. The lumens of some capillary vessel of glomerule are narrow or even blocked. The related epithelial cells have proliferated and the basementmembrane has shrunk, mesentery cells and groundsubstance are of no obviously hyperplasia.

The H Group: There are plenty of lysosomes and unequal vacuoles in the cytoplasm of the renal tubule epithelial cells. A little few of the epithelial cells are with cytoplasm crystals. Microvilli are swelling and the mesenchyme was infiltrated with lymphocytes. The mesenchyme crystals and fibrous cell hyperplasia are obviously lighter than that of the model control group. The capillary vessels of glomerule are open; there is no obviously hyperplasia of the epithelial cells, the endothelial cells and the basementmembrane. The mesentery cells and the groundsubstance are not multiplied.

The M Group: A few renal tubule epithelial cells is swelling. Some local microvilli are swelling and drop off. The caryon heterochromatin increases and tends to pycnosis. mesenchyme is infiltrated by lymphocyte and with a few mesenchyme crystal. The capillary vessel of glomerule is open. There is no obviously hyperplasia with epithelial cells. The basementmembrane is no obviously thickening and without compact complex deposition. The epithelial cells are swelling and with hyperplasia in some region. The mesentery is without enlargement, and the mesentery cells and groundsubstance are no obviously hyperplasia.

The L Group: There are medium quantity of lysosomes in the renal tubule epithelial cells. Few caryons of the renal tubule epithelial cell are abnormality. The caryon heterochromatins are obviously multiplied and appear to be like massive, tending to pycnosis. There are unequal vacuoles appearing in the cytoplasm mesenchyme was infiltrated by a few lymphocyte. The capillary vessel of glomerule is open. Some of the epithelial cells are swelling, the basementmembrane is not obviously thickening and without compact complex deposition, epithelial cells are swelling and with hyperplasia in some regions, the feet process there fuse. The mesentery is without enlargement. The mesentery cells and groundsubstance are no obviously proliferation.

Shenkangning Group: The lysosomes in the renal tubule epithelial cells are obviously increased. Some epithelial cells are with crystal deposition and few of them were degrading, necrosis or falling off. The basementmembrane shrinks and many unequal vacuoles can be seen. The mesenchyme was infiltrated by lymphocyte and crystal deposition. The capillary vessel of glomerule is open and few of epithelial cells of capillary vessel have proliferated. The basementmembrane is not obviously thickening and without compact complex deposition. The mesenteric and groundsubstance have no obviously hyperplasia.

From the results of optical and electronical microscope we know that there is degeneration, necrosis and fiberosis of mesenchyme in the renal tubule after feeding with adenine, while the pathologic change of the glomerule is relatively gently. The results under both optical and electronical microscope show that the pathologic change of the treatment group with the invented medicine was lighter than that of the model control group and the shenkangning group. It proved the invented medicine have the better function to inhibit the dilatation of the renal tubules and the fibrosis of mesenchyme caused by adenine, and improve the recovery of the epithelial cells in the renal tubule and the hyperplasia of mitochondria.

(II) The effect on the Rat with CRF Caused by the Ablate of ⅚ Kidney

1, Normal Condition, Body Weight and Kidney Index that, 4 weeks after the second resection, the CRF rat model was built. After fed with the invented medicine, the rise of weight in the H group is more than the model control group and the positive medicine control group (P<0.05). Put the rat to death after 6 weeks therapy, the remnant kidney was obviously larger than that before the therapy. The kidney indexes of the H group and M group were slightly less than the model control group and the normal control group. But there was no significant difference.

During the experiment, the model control group, M group and Shenkangning group had 2 rats died each, while H group and L group had 1 rat death each. From the anatomy of all

TABLE 17

The invented medicine's effects on the weight and kidney index of the CRF rat caused by ⅚ nephrectomy

| Group | Dose (g/kg, Weight) | Weight (g, $\overline{X} \pm S$) | kidney Weight (g, $\overline{X} \pm S$) | kidney index (mg/g Weight, $\overline{X} \pm S$) |
|---|---|---|---|---|
| Normal control | — | 419.20 ± 54.09 (10) | 1.21 ± 0.12 (10) | 2.85 ± 0.27 (10) |
| Model control | — | 294.86 ± 17.41 (8) | 2.21 ± 0.48 (8) | 7.46 ± 1.40 (8) |
| H group | 43.30 | 335.63 ± 38.06*△ (9) | 2.01 ± 0.48 (9) | 6.21 ± 2.28 (9) |
| M group | 21.65 | 349.60 ± 41.80*△ (8) | 2.48 ± 0.42 (8) | 7.21 ± 1.82 (8) |
| L group | 10.83 | 302.82 ± 38.63 (9) | 2.33 ± 0.23 (9) | 7.78 ± 0.93 |
| Shenkangning | 10.38 | 288.16 ± 18.41 (8) | 2.11 ± 0.16 (8) | 7.36 ± 90.76 (8) |

*Comparing with the model control group, P < 0.05
△Comparing with the positive medicine control group, P < 0.05

When the rat was resected ⅚ of the kidney, it gradually appeared the reduce of foodentake. The rat's fur was dry and lack of luster. Its ears and tail looked pale. The syndromes aggravated along the time and the rise of the weight is obviously slower than the normal group. It had been proved the dead rats, it showed that all the kidneys were obviously swelling, stiff, and appeared brown, without any abnormity of the other organs.

2, BUN and Scr

TABLE 18

The invented medicine's effects on the kidney's function of the CRF rat caused by ⅚ nephrectomy

| Group | Dose (g/kg Weight) | BUN(mmol/L, $\overline{X} \pm S$) | | Scr(umol/L, $\overline{X} \pm S$) | |
|---|---|---|---|---|---|
| | | Before the treatment | After the treatment | Before the treatment | After the treatment |
| Normal control | — | 9.97 ± 0.77 (10) | 8.16 ± 1.44 (10) | 72.57 ± 6.73 (10) | 70.79 ± 3.04 (10) |
| Model control | — | 16.81 ± 2.46 (10) | 23.12 ± 6.97 (8) | 98.63 ± 6.61 (10) | 108.83 ± 12.60 (8) |
| H group | 43.30 | 17.42 ± 1.47 (10) | 19.59 ± 4.25 (9) | 98.28 ± 7.56 (10) | 85.90 ± 7.75*△ (9) |
| M group | 21.65 | 16.93 ± 1.41 (10) | 19.63 ± 3.27 (8) | 99.59 ± 8.32 (10) | 89.34 ± 4.99* (8) |
| L group | 10.83 | 18.20 ± 4.01 (10) | 22.96 ± 3.81 (9) | 101.06 ± 13.45 (10) | 98.29 ± 10.79 (9) |
| Shen-kangning | 10.38 | 17.06 ± 2.20 (10) | 20.27 ± 5.45 (8) | 96.67 ± 8.86 (10) | 97.54 ± 8.78 (8) |

*Comparing with the model control group, P < 0.05
△Comparing with the shenkangning control group, P < 0.05

Before the therapy, BUN and SCR of every model group were obviously higher than that of the normal control group ($P<0.01$), there was no significant difference between the model groups ($P>0.05$). After 6 weeks therapy, BUN and SCR of every model group were still increasing, while the increasing of the BUN and SCR was obviously inhibited in the H group and M group comparing with the other model group ($P<0.05$).

3, Hb and Serum Proteins obviously difference between the other model groups on the cholesterol and Triglyceride ($P>0.05$).

5. Observation of Pathomorphology (1) General Pathologic Change a. The General Change of Kidney The shape of the kidney of model groups was irregularity, swelling, gray and yellow colored, stiff, the renal cortex-medulla border on the crosssection was not clear. The swelling levels of the kidneys in all the treatment groups

TABLE 19

The invented medicine's effects on the Hb, TP, ALB of the CRF rat caused by 5/6 nephrectomy

| Group | Dose (g/kg Weight) | Hb(g/L, $\bar{X} \pm S$) Before the treatment | After the treatment | TP(g/L, $\bar{X} \pm S$) Before the treatment | After the treatment | ALB(g/L, $\bar{X} \pm S$) Before the treatment | After the treatment |
|---|---|---|---|---|---|---|---|
| Normal control | — | 164.70 ± 5.42 (10) | 165.00 ± 5.40 (10) | 79.09 ± 3.61 (10) | 74.60 ± 5.70 (10) | 57.12 ± 2.99 (10) | 50.50 ± 2.64 (10) |
| Model control | — | 133.02 ± 5.26 (10) | 143.75 ± 6.32 (8) | 64.24 ± 7.22 (10) | 58.63 ± 3.78 (8) | 38.64 ± 4.46 (8) | 34.63 ± 3.11 (8) |
| H group | 43.30 | 130.70 ± 5.59 (10) | 151.00 ± 10.54*Δ (9) | 66.77 ± 2.08 (10) | 64.56 ± 5.15*Δ (9) | 50.46 ± 3.89 (10) | 43.11 ± 4.31*Δ (9) |
| M group | 21.65 | 134.12 ± 3.50 (10) | 148.88 ± 11.01*Δ (8) | 71.09 ± 3.69 (10) | 63.75 ± 6.11*Δ (8) | 47.75 ± 7.76 (10) | 44.13 ± 6.73*Δ (8) |
| L group | 10.83 | 130.27 ± 4.36 (10) | 144.89 ± 19.70 (9) | 69.55 ± 6.86 (10) | 61.44 ± 5.77 (9) | 43.06 ± 6.67 (10) | 38.90 ± 5.06 (9) |
| Shen-kangning | 10.38 | 128.75 ± 7.34 (10) | 128.00 ± 11.55 (8) | 67.31 ± 3.93 (10) | 56.63 ± 6.93 (8) | 50.67 ± 4.40 (10) | 36.50 ± 3.07 (8) |

*Comparing with the model control group, $P < 0.05$
ΔComparing with the shenkangning group, $P < 0.05$ Before the therapy, Hb and plasma protein of every model group was obviously lower than the normal level; after the therapy, Hb and plasma protein of the H group and the M group were obviously higher than the model control group and shenkangning group, there was significant difference between them with Hb, TP and ALB ($P<0.05$).

Blood Fat Variation were lighter than that of the control groups more or less. The color in the treatment groups were deepening to tawny.

b. The Change of the Glomerule

The pathological changes of the glomerule under, the optical microscope were different, such as: the compensating dilatation of the glomerule, the different degrees hyperplasia of the mesentery cells and the groundsubstance, the

TABLE 20

The invented medicine's effects on the blood fat of the CRF rat caused by 5/6 nephrectomy

| Group | Dose (g/kg Weight) | Cholesterol (mmol/L, $\bar{X} \pm S$) Before the treatment | After the treatment | Triglyceride (mmol/L, $\bar{X} \pm S$) Before then treatment | After the treatment |
|---|---|---|---|---|---|
| Normal control | — | 1.93 ± 0.13 (10) | 1.62 ± 0.12 (10) | 0.86 ± 0.07 (10) | 0.84 ± 0.16 (10) |
| Model control | — | 3.11 ± 0.24 (10) | 5.15 ± 0.35 (8) | 0.85 ± 0.09 (10) | 3.55 ± 0.47 (8) |
| H group | 43.30 | 3.10 ± 0.16 (10) | 3.94 ± 0.45* (9) | 0.98 ± 0.14 (10) | 2.56 ± 0.41 (9) |
| M group | 21.65 | 3.34 ± 0.29 (10) | 4.09 ± 0.39 (8) | 1.22 ± 0.19 (10) | 2.48 ± 0.59 (8) |
| L group | 10.83 | 3.17 ± 0.24 (10) | 4.90 ± 0.58 (9) | 1.02 ± 0.09 (10) | 2.49 ± 0.37 (9) |
| Shen-kangning | 10.38 | 3.29 ± 0.19 (10) | 4.11 ± 0.73 (8) | 0.85 ± 0.14 (10) | 3.15 ± 0.24 (8) |

*Comparing with the model control group, $P < 0.05$

The plasma cholesterol of each model group was higher than the normal group ($P<0.05$). After the therapy, the plasma cholesterol of the H group was obviously lower than that of the model control group ($P<0.05$), there was no obstruction of the lumen of capillary vessel, the fusion of the renal capsule and polymorphic glomerule with vitreous degeneration. According to the histology classification criteria of the illed glomerule provided by Purkerson. et, account the percentage of each grade glomerule of the different group.

TABLE 21

The invented medicine's effects on the pathological changes of glomerule of the CRF rat caused by ⅚ nephrectomy (%)($\bar{X} \pm S$)

| Group | Dose (g/kg Weight) | dilatation of glomerule | 0Grade | I Grade | II Grade | III Grade | III Grade |
|---|---|---|---|---|---|---|---|
| Normal control | — | 3.00 ± 0.70 | 90.36 ± 1.40 | 6.64 ± 1.70 | 0 | 0 | 0 |
| Model control | — | 32.80 ± 0.90 | 9.30 ± 2.40 | 11.20 ± 3.60 | 13.60 ± 0.78 | 20.90 ± 0.80 | 12.20 ± 3.10 |
| H group | 43.30 | 13.40 ± 0.50**Δ | 22.30 ± 0.56 | 24.60 ± 1.70 | 19.80 ± 0.44 | 11.30 ± 2.80 | 8.60 ± 2.70 |
| M group | 21.65 | 17.90 ± 0.20*Δ | 16.90 ± 2.40 | 20.30 ± 0.80 | 20.40 ± 0.98 | 14.70 ± 1.70 | 9.80 ± 1.32 |
| L group | 10.83 | 28.40 ± 0.40 | 13.80 ± 0.80 | 10.60 ± 2.80 | 14.80 ± 0.86 | 20.60 ± 1.80 | 11.80 ± 0.87 |
| Shenkang-ning | 10.38 | 12.40 ± 0.76 | 11.80 ± 2.80 | 15.60 ± 0.49 | 18.60 ± 2.50 | 12.00 ± 0.17 | |

*Comparing with the model control group, $P < 0.01$,
ΔComparing with shenkangning group, $P < 0.05$ By comparing the pathological changes of glomerule in each group, it was found that the dilatation of glomerule of the model groups was obviously higher than the normal control group ($P<0.01$), while the dilatation of glomerule in H group and M group was obviously less than the model control group and the shenkangning group ($P<0.05$ or $P<0.01$). The proportion of above III grade pathological changes of glomerule in model control group is higher than that of the H group and M group, the majority of pathologic change grade in the H group and M group is 0, I and II grade. This condition is remarkably different to the other groups ($P<0.05$). The pathological change of glomerule of XV grade was on a low percent in all the model groups. Each model group had different degree of increase with the groundsubstance and cells of glomerule's mesentery. Some of the glomerule appeared segmental sclerosis, capsule adhesion or the full glomerule sclerosis. Some capillary vessel of sclerous glomerule with collapse, stenosis or obstruction, the above pathological changes was slightly in the H group and M group, comparing with the other groups.

This showed that the invented medicine could relieve the hypertrophy and sclerosis of the kidney.

C. The Changes of Renal Tubules and Mesenchyme

The renal tubules of each model group had dilatation, the epithelial cells of renal tubular were of atrophia, degeneration, necroses or falling off. There were different degrees of fiberosis and inflammation cell infiltration in the renal mesenchyme. There was different degree relief of the above pathological changes in the treatment groups, the result is in TABLE 22.23

TABLE 22

The invented medicine's effects on the pathological changes of renal tubules of the CRF rat caused by ⅚ nephrectomy (%)($\bar{X} \pm S$)

| Group | Dose (g/kg Weight) | 0 Grade | I Grade | II Grade | III Grade |
|---|---|---|---|---|---|
| Normal control | — | 92.30 ± 0.27 | 6.80 ± 1.10 | 0 | 0 |
| Model control | — | 5.00 ± 0.86 | 14.80 ± 0.79 | 36.10 ± 1.86 | 44.80 ± 2.40 |
| H group | 43.30 | 20.00 ± 0.71 | 53.20 ± 0.29 | 14.80 ± 0.88 | 13.10 ± 0.76 |
| M group | 21.65 | 15.00 ± 0.88 | 52.30 ± 0.90 | 21.50 ± 1.30 | 22.80 ± 1.68 |
| L group | 10.83 | 14.70 ± 0.77 | 21.20 ± 0.85 | 32.10 ± 0.90 | 41.20 ± 2.50 |
| Shenkangning | 10.38 | 15.20 ± 0.34 | 31.80 ± 0.96 | 26.50 ± 1.75 | 20.60 ± 0.38 |

The impairment in the renal bubule of each model group was obvious. The difference was significant comparing with the normal control groups ($P<0.01$); the pathological changes was slight in the H group and the M group comparing with the other model groups, and most of them is I grade. There was remarkable difference comparing with the other model control groups ($P<0.05$)

TABLE 23

The invented medicine's effects on the pathological changes of renal mesenchyme of the CRF rat caused by 5/6 nephrectomy (%)($\bar{X} \pm SD$)

| Group | Dose (g/kg Weight) | 0 Grade | I Grade | II Grade | III Grade |
|---|---|---|---|---|---|
| Normal control | — | 86.80 ± 0.34 | 13.20 ± 3.20 | 0 | 0 |
| Model control | — | 4.86 ± 0.22 | 24.80 ± 0.17 | 56.70 ± 1.10 | 13.70 ± 1.80 |
| H group | 43.30 | 15.40 ± 2.67 | 48.80 ± 2.20 | 30.20 ± 1.10 | 5.60 ± 2.40 |
| M group | 21.65 | 11.30 ± 0.28 | 34.80 ± 0.88 | 43.70 ± 1.52 | 10.20 ± 0.97 |
| L group | 10.83 | 9.20 ± 0.34 | 31.40 ± 1.20 | 52.20 ± 0.90 | 8.20 ± 0.97 |
| Shenkangning | 10.38 | 10.80 ± 2.56 | 24.70 ± 2.80 | 53.20 ± 1.80 | 11.30 ± 0.88 |

The fiberosis with the renal mesenchyme of each model group was obviously, there was remarkable difference comparing with the normal control groups (P<0.01); the pathological chances of each group focused in I, II grade, most of the pathological changes of the H group and the M group was I grade. There was predominance difference comparing with the other model control groups (P<0.05)

(2) The Change of the Kidney's Ultrastructure

Normal Control Group:

The capillary vessel of glomerule is open, there is a few of red blood cells in the blood vessel and the vessel wall is lining with fenestra type endothelial cell, without swelling and hyperplasia. The basement membrane is even and without deposition of the compact complex. The thickness of the basement membrane is 110-60 nm (normal). The epithelial cells are also without swelling and vacuolar degeneration, whose foot processes are sharp. The mesentery is without enlargement. No cell hyperplasia, groundsubstance multiply or compact complex deposition is found. The epithelial cells of the renal tubule are of no obvious change and belong to the normal nephridial tissue.

Model Control Group:

The lumen of some capillary vessel of glomerule was complete or incomplete obliteration because of the hyperplasia and swelling of endothelial cells. The endothelial cells in the lumen of some capillary vessel of glomerule were swelling and appeared to microvillus shape, the basementmembrane was not obviously thickening and without compact complex deposition. The pathological changes of epithelial cells were obviously, appeared as the vacuolization and swelling, a wide range of feet process were confluens. The lysosomes of cytoplasm were increased. The mesentery had enlarged; mesentery cells and groundsubstance were of obviously hyperplasia and infiltration by foam cells that could phagocytize lipid in some regions. The necrosis of renal tubular was invisible, but the epithelial cell of renal tubular was of swelling, vacuolization. The lysosomes were obviously increased.

The H Group: The capillary vessel of glomerule was open; few endothelial cells were of hyperplasia and swelling. The lumen appeared as stenosis. The basementmembrane was no obviously thickening and without compact complex deposition. Few epithelial cells were of swelling and appeared as vacuolization and slightly microvillus. The mesentery was without enlargement. The mesentery cells and groundsubstance were of no obvious hyperplasia and compact complex deposition. The necrosis of endothelial cell was invisible. The pathological changes of glomerule, renal tubular and mesenchyme in this group was obviously slighter comparing with the model control and the shenkangning group.

The M Group: Some of the capillary vessel of glomerule was open. Few lumens of capillary vessels were of narrowing or incomplete obliteration because of the hyperplasia and swelling of the endothelial cells. Few endothelial cells were with vacuolization, the basementmembrane was of no obviously thickening and without compact complex deposition. The epithelial cells were of vacuolization and swelling. A wide range of feet process fused. The lysosomes in the cytoplasm increased. The Mesentery enlarged and groundsubstance multiplied; Few of mesentery cells were of hyperplasia. The pathological changes of renal tubules were slight. The pathological changes of the M group were slight comparing with the model control and the shenkangning group.

The L Group: The capillary vessels of glomerule were open. Few endothelial cells were of swelling and appeared as vacuolization and microvillus. Most endothelial cells of the capillary vessels were with no obviously change. The basementmembrane was no obviously thickening and without compact complex deposition. Most epithelial cells were of no obviously changes, few of which appeared as swelling, slightly microvillus and a limited range of foot process fusion. Most mesentery with no obviously changes, a few mesentery cells with hyperplasia, there was a few lysosome in the epithelial cells of renal tubules, which was slight comparing with the model control group.

Shenkangning Group: The capillary vessels of glomerule were open. Few lumens of capillary vessel were narrowing because of the swelling of endothelial cells, the neutrophil leucocytes and lymphocytes were common in the lumen of the capillary vessels, the capillary vessels and the basementmembrane were of no obviously thickening and without compact complex deposition. The epithelial cells appeared of swelling, the feet process fused and turned into microvillus like. The lysosomes of cytoplasm increased. Few mesenteries enlarged and the groundsubstance obviously multiplied. The pathological changes of renal tubules were slight and no necrosis was visible.

The data above proved that the invented medicine especially at the high dose could improve the ultrastructure of the kidney obviously.

Result: In this experiment the CRF rats caused by adenine intake were treated by feeding the invented medicine on high dose, middle dose and low dose for 6 weeks. It proved that the invented medicine could decrease the BUN, Scr obviously. The curative effect was better than the normal control group and the positive medicine control group (shenkangning group) (P<0.01 and P<0.05). What's more, the invented medicine could improve the Hb and the plasma protein content. This invented medicine had a obvious effect to inhibit the dilation of the renal tubules and the interstitial fibrosis, benefit the renal tubules epithelial cells' repairing and the mitochondrion's multiplying. Building the CRF model by 5/6 nephrectomy, the Scr and BUN 4 weeks after the second operation were higher than that of the normal group (P<0.05). The plasma protein and the Hb were lower than the normal group (P<0.05). The general pathological change was the rest kidney enlarging; The renal glomerulus enlarged for compensation and The mesenteries proliferation on the light to middle level were the main changes under the optical microscope. The impairment, the necrosis and the block of the renal tubule could be found. There also was renal interstitial fibrosis; Under the electronic microscope the pathologic changes were that: the narrowing of the renal glomerulus capillary vessels, the swelling and the microvillus-like changing of the endothelial cells, the proliferation of the endothelial cells, the fusion of the feet process, the enlargement of the mesenteries, multiplying of the mesenteries' matrix and the impairment of the renal tubule. All the change belongs to the pathological change of the renal glomerulus cirrhosis.

The pathologic change proved that the animal model was fit for the CRF behavior. After feeding the CRF rats with the invented medicine for 6 weeks on the high dose and the middle dose, the therapy decreased the BUN and Scr remarkably. The effect was better than the model control group and the shenkangning group, BUN: there was remarkable difference between the H group, M groups and the model control group, shenkangning group. Scr: there was remarkable difference between the H group and the model control group and shenkangning group. This medicine could improve the Hb (P<0.05). The pathologic observe indicated that the invented medicine could inhibit the over hypertrophy of the renal glomerulus, the proliferation of the mesenteries cells, mesenteries matrix, the cirrhosis of the renal glomerulus, and the interstitial fibrosis of the renal tissue.

In short, by the pharmacodynamics experiment on the two types of CRF rats, the result indicated that the invented medicine could lower the Scr, BUN, improve the Hb, TP. According the indexes, M group had the best synthetic curative effect and the H group was better than the L group. The mechanism was related to the medicine's functions on relieving the impairment on renal glomerulus, inhibiting the cirrhosis of the renal glomerulus, repairing and improve the renal interstitial impairment.

EXECUTION EXAMPLE 1

| Prepared fleece-flower root | 400 g; | Dodder | 200 g |
| pseudostellaria root | 600 g | Prepared atractylodes rhizome | 120 g |
| wolfberry fruit | 400 g | Achyranthes root | 400 g |
| lycopus herb | 400 g | red peony root | 400 g |
| indian bread | 600 g | alisma rhizome | 400 g |
| psyllium seed | 600 g | Prepared rhubarb | 240 g |

Take the prepared fleece flower root and the prepared rhubarb then crush them in to raw flour, use 70% alcohol as the dissolvent, after 24 hours soakage, percolation with the speed of 2 ml/min, collect the percolate about 5.12 L then retrieve the alcohol, condense to proper amount to get the fluidextract; take atractylodes rhizome and crush it into raw flour, put the raw flour into the water 5 times of it for 4 hours, then distill the mixture to get the volatile oil from the vapor, keep the gruffs and the solution alone; dissolve the volatile oil into proper amount alcohol then on the method of colloid mill grind the mixture to package the volatile oil. The ratio of volatile oil solution to β-dextrin is 1:8 and the ratio of β-dextrin and water is 1:2, grinding surface is 5 μm, grinding speed is 3000 round/min, After 15 minutes grind, the mash is made, dehydrate it below 40° C. and then crush it into powder to get the clathrate; Cook the wolfberry fruit and indian bread in the water 3 times and every time is 2 hours, the amount of the water is 8 times weight of the two herbs. Combine all the cooked water together then concentrate it to the relative density is 1.10 under 80° C., do the centrifugation to get the centrifugate; put the prepared atractylodes rhizome's gruffs, solution and the rest 7 of the herbs together, cook the mixture in the water for 2 times, each time is 2 hours and the water is 8 times weight of the mixture. Mingle all the cooked water and filtrate it. Concentrate the filtrated water to the relative density is 1.15 under 80° C., then cool it down to the room temperature. Add alcohol to this solution until the alcohol's concentration up to 65%, standing the mixture 24 hours to get the supernate solution, Retrieve the alcohol from the supernate solution and put the rest of it with the fluid extract (rhubarb, fleece-flower root) and the centrifuged extract (wolfberry fruit and fl), concentrate the mixture to the relative density is 1.30 under 80° C. and vacuum degree is −0.09 MPa, dehydrate it in a low pressure and under 80° C., then crush the dry extract into fine powder. Mingle the fine powder, the volatile oil clathrate and the adjuvant together, pressing to get 1000 tablet, each one contains 4.76 g crude drug, coating it with thin membrane.

EXECUTION EXAMPLE 2

| fleece-flower root | 500 g | dodder | 250 g |
| pseudostellaria root | 600 g | atractylodes rhizome | 150 g |
| wolfberry fruit | 500 g | Achyranthes root | 500 g |

Take the prepared fleece flower root and the prepared rhubarb then crush them in to raw flour, use 70% alcohol as the dissolvent, after 24 hours soakage, percolation with the speed of 2 ml/min, collect the percolate about 5.12 L then retrieve the alcohol, condense to proper amount to get the fluidextract; take atractylodes rhizome and crush it into raw flour, put the raw flour into the water 5 times of it for 4 hours, then distill the mixture to get the volatile oil from the vapor, keep the gruffs, volatile oil and the solution alone; Cook the wolfberry fruit in the water 3 times and every time is 2 hours, the amount of the water is 9 times weight of it. Combine all the cooked water together then concentrate it to the relative density is 1.10 under 80° C., do the centrifugation to get the centrifugate; put the atractylodes rhizome's gruffs, solution and the rest herbs together, cook the mixture in the water for 2 times, each time is 2 hours and the water is 8 times weight of the mixture. Mingle all the cooked water and filtrate it. Concentrate the filtrated water to the relative density is 1.15 under 80° C., then cool it down to the room temperature Add alcohol to this solution until the alcohol's concentration up to 65%, standing the mixture 24 hours to get the supernate solution, Retrieve the alcohol from the supernate solution and put the rest of it with the fluid extract from fleece-flower root and the centrifuged extract from wolfberry fruit, concentrate the mixture to the relative density is 1.30 under 80° C. and vacuum degree is −0.09 MPa, dehydrate it in a low pressure and under 80° C., then crush the dry extract into fine powder. Mingle the fine powder, the volatile oil clathrate and the adjuvant together, to get 1000 capsules, each one contains 2.5 g crude drug.

EXECUTION EXAMPLE 3

| Prepared fleece-flower root | 500 g | dodder | 200 g |
| pseudostellaria root | 300 g | Prepared atractylodes rhizome | 100 g |
| wolfberry fruit | 400 g | Achyranthes root | 400 g |
| lycopus herb | 200 g | red peony root | 200 g |
| indian bread | 300 g | alisma rhizome | 200 g |
| psyllium seed | 300 g | Prepared rhubarb | 100 g |

Make the above raw material into 1000 capsules with routine technology.

EXECUTION EXAMPLE 4

| fleece-flower root | 500 g | dodder | 200 g |
| pseudostellaria root | 300 g | atractylodes rhizome | 100 g |
| wolfberry fruit | 400 g | Achyranthes root | 400 g |
| lycopus herb | 200 g | red peony root | 200 g |
| indian bread | 300 g | alisma rhizome | 200 g |
| Psyllium seed | 300 g | rhubarb | 100 g |

Make the above raw material into oral liquid with routine technology.

The invention claimed is:

1. A pharmaceutical composition for treating CRF, which consists of the herbs based on weight proportion as follows:

| fleece-flower root | 100-600 part-by-weight |
| cuscuta seed | 100-600 part-by-weight |
| pseudostellaria root | 100-600 part-by-weight |
| atractylodes rhizome | 100-600 part-by-weight |
| wolfberry fruit | 100-600 part-by-weight |
| achyranthes root | 100-600 part-by-weight. |

2. The composition according to claim 1, wherein the weights of the herbs are as follows:

| fleece-flower root | 500 g | dodder | 250 g |
| pseudostellaria root | 600 g | atractylodes rhizome | 150 g |
| wolfberry fruit | 500 g | achyranthes root | 500 g. |

3. The composition according to claim 1, wherein the fleece-flower root is prepared fleece-flower root, the atractylodes rhizome is prepared atractylodes rhizome, or the composition further includes 100-600 parts by weight prepared rhubarb, or a combination thereof.

4. A method for reducing blood urea nitrogen (BUN) and serum creatinine (Scr), inhibiting cirrhosis of renal glomerulus, repairing and improving damage of the renal mesenchyme comprising administering a pharmaceutical composition of claim 1 to a patient in need thereof.

5. A testing method for tablets made from the pharmaceutical composition according to claim 1, which comprises the following steps:

provide 10 pieces of tablet made from the pharmaceutical composition according to claim 1 and remove the coats of them, weigh them precisely and triturate them to fine powder; add 1 g of the fine powder to 25 mL of 2.5 mol/L sulfuric acid and 40 mL chloroform in a 250 mL round bottomed flask; perform backflowing extraction on a water bath for 4 hours, separate the resulting chloroform layer; then add 40 mL chloroform into the flask to extract the residue; perform backflowing extraction again for 3 hours, separate the resulting chloroform layer; and extract the remaining residue 3 times, using 10 mL chloroform for each time and separating the resulting chloroform layer each time; mix all 5 of the separated chloroform extract layers, and wash the resulting mixture with water until its pH reaches neutrality; recover the chloroform from the neutral solution, dissolve the residue with methanol; the methanol solution is adjusted to 5 mL to serve as the test sample; dissolve emodin in methanol directly to prepare a 0.1 mg/mL emodin-methanol solution to serve as the control sample; carry out a method of thin layer chromatography, imbibe the test solutions 5 µl, the control solution 2 µl and 8 µl, then drop them to the same silica gel G thin layer separately; using benzene-ethylacetate-methanol-methanoic acid-water (3:1:0.2:0.05:0.5) as the developing agent, after the developing agent has migrated to 10 cm in the plate, take out the plate from the developing agent and dry it in the air; carry out a scan method of the thin layer chromatography, scan the spots in the chromatogram under visible light at these wavelengths: $\lambda_S$=435 nm, $\lambda_R$=600 nm; measure and calculate the absorbance quantity of the test solution, then compare it with the absorbance quantity of the control solution and calculate to get the content of the test solution; whereby the content of emodin in each tablet is not permitted to be lower than 0.07 mg.

6. An identification method for tablets made from the pharmaceutical composition according to claim 1, which comprises the following steps:

provide tablets made from the pharmaceutical composition according to claim 1;

A. take 5 pieces of tablet and triturate them into fine powder, perform backflowing extraction of the powder with 30 mL chloroform for 1 hour; filter and evaporate the filtrate; perform backflowing extraction of the residue with 40 mL alcohol for 1 hour; filter and evaporate the filtrate to dry; dissolve the residue in 1 mL alcohol to serve as the test solution; take 1 g of fleece-flower root as reference herb, make the herb into the reference solution in the same way just described immediately above in this subpart (A); carry out a method of thin layer chromatography; imbibe 5 µL of the two kinds of solutions and drop the solutions on the same silica gel G thin layer plate separately; use aceticether-methanol-water (100:17:13) mixture as the developing agent; after the developing agent has migrated to 10 cm in the plate, take out the plate from the developing agent and dry it in the air; examine the plate under ultra-violet light at the wavelength of 365 nm, the fluorescent spots in the chromatogram of the test solution should correspond in position and color to the spots in the chromatogram of the control solution;

B. take another 4 pieces of tablet and triturate them into fine powder, perform backflowing extraction of the powder with 30 mL alcohol for 30 minutes; filter and add 2 mL hydrochloric acid to the filtrate to make a mixture solution, perform backflowing extraction of the mixture solution for 1 hour, then concentrate the solution to about 2 mL, add 5 mL water to it and extract the new solution in 15 mL chloroform for 2 times; evaporate the chloroform extract solution to dry, dissolve the residue in 2 mL chloroform to serve as the test solution; dissolve oleanolic acid in methanol at a concentration of 1 mg/mL to serve as the control solution; according to a method of thin layer chromatography, imbibe 5 µL of the two solutions and drop them to the same silica gel G thin layer plate separately, and use chloroform-acetone (1:1) as the developing agent; after developing, take out the thin layer plate from the developing agent and dry it in the air; spray a 10% vitriolic-acid-alcohol solution to the thin layer plate, and then blow the thin layer plate with hot air until the spots in the plate become clear; the spots in the chromatogram of the test solution should correspond in position and color to the spots in the chromatogram of the control solution; and C. take another 5 pieces of tablet and dissolve them in 30 mL methanol and perform backflowing extraction thereof for 30 minutes; filter and evaporate the filtrate to dry; dissolve the residue in 15 mL water, extract the water solution with n-butyl alcohol saturated by water for 2 times with shaking, using 15 mL of the n-butyl alcohol for each time; mix the resulting n-butyl alcohol extract solutions and evaporate n-butyl alcohol to dry; dissolve the residue in methanol to 1 mL to serve as the test solution; prepare a paeoniflorin-methanol solution at a concentration of 1 mg/mL as the control solution; according to a method of thin layer chromatography, imbibe 5 µL of the two solutions and drop them to the same silica gel G thin layer separately, and use chloroform-ethylacetate-methanol-methanoic acid (40:5:10:0.2) as the developing agent, after developing, take out the thin layer plate from the developing agent and dry it in the air; spray 10% vitriolic-acid-alcohol solution to the thin layer plate, and then blow the thin layer plate with hot air until the spots in the plate become clear; the spots in the chromatogram of the test solution should correspond in position and color to the spots in the chromatogram of the control solution.

7. A pharmaceutical composition for treating CRF, which consists of the herbs based on weight proportion as follows:

| | |
|---|---|
| fleece-flower root | 100-600 part-by-weight |
| cuscuta seed | 100-600 part-by-weight |
| pseudostellaria root | 100-600 part-by-weight |
| atractylodes rhizome | 100-600 part-by-weight |
| wolfberry fruit | 100-600 part-by-weight |
| achyranthes root | 100-600 part-by-weight |
| lycopus herb | 100-600 part-by-weight |
| red peony root | 100-600 part-by-weight |
| Poria | 100-600 part-by-weight |
| alisma rhizome | 100-600 part-by-weight |
| Asiatic plantain seed | 100-600 part-by-weight |
| rhubarb | 100-600 part-by-weight. |

8. The composition according to claim 7, wherein the weights of the herbs are as follows:

| | | | |
|---|---|---|---|
| fleece-flower root | 400 g | cuscuta seed | 200 g |
| pseudostellaria root | 600 g | atractylodes rhizome | 120 g |
| wolfberry fruit | 400 g | achyranthes root | 400 g |
| lycopus herb | 400 g | red peony root | 400 g |
| Poria | 600 g | alisma rhizome | 400 g |
| Asiatic plantain seed | 600 g | rhubarb | 240 g. |

9. The composition according to claim 7, wherein the weights of the herbs are as follows:

| | | | |
|---|---|---|---|
| fleece-flower root | 500 g | cuscuta seed | 200 g |
| pseudostellaria root | 300 g | atractylodes rhizome | 100 g |
| wolfberry fruit | 400 g | achyranthes root | 400 g |
| lycopus herb | 200 g | red peony root | 200 g |
| Poria | 300 g | alisma rhizome | 200 g |
| Asiatic plantain seed | 300 g | rhubarb | 100 g. |

10. The composition of claim 7 wherein the rhubarb is prepared rhubarb.

11. A method for preparing a pharmaceutical composition comprising the steps as follows:
I. providing the herbs:

| | |
|---|---|
| fleece-flower root | 100-600 part-by-weight |
| cuscuta seed | 100-600 part-by-weight |
| pseudostellaria root | 100-600 part-by-weight |
| atractylodes rhizome | 100-600 part-by-weight |
| wolfberry fruit | 100-600 part-by-weight |
| achyranthes root | 100-600 part-by-weight |
| lycopus herb | 100-600 part-by-weight |
| red peony root | 100-600 part-by-weight |
| alisma rhizome | 100-600 part-by-weight |
| asiatic plantain seed | 100-600 part-by-weight |
| rhubarb | 100-600 part-by-weight |
| Poria | 100-600 part-by-weight |

II. preparing steps as follows:
A. crush fleece flower root and rhubarb into coarse powder, and percolate with 60%-90% alcohol as solvent by soaking the powder in the solvent and permitting the solvent to percolate; collect the percolate, retrieve the alcohol in the percolate, then condense the percolate until forming a liquid extract;

B. crush atractylodes rhizome into coarse powder, soak the coarse powder in 2-8 times by weight of water for 2-8 hours, isolate a volatile oil from the atractylodes rhizome powder by distillation; collect the aqueous extract solution and residue in another container; dissolve the volatile oil in 60%-90% by weight alcohol, and grind the resulting mixture with β-cyclodextrin and water together in a colloid mill, wherein the ratio of volatile oil to β-cyclodextrin is 1:4-10 and the ratio of β-cyclodextrin to water is 1:1-3, to form a paste; dry the paste and crush it into powder to get an inclusion compound of the volatile oil;

C. cook the wolfberry fruit and tuckahoe with 6-10 times by weight of water and repeat up to 3 times, at 1-3 hours for each time; mix the cooked solutions together, condense and centrifugate the mixed cooked solutions, collect the centrifugate for further use;

D. mix the residue of atractylodes rhizome after distillation in step B with the remaining herbs: cuscuta seed, pseudostellaria root, *achyranthes* root, lycopus herb, red peony root, poria, alisma rhizome, and asiatic plantain seed; cook them with 6-10 times by weight of water for up to 3 times, 1-2 hours for each time; collect the cooked solutions, mix the cooked solutions, filter the mixed cooked solutions, condense the filtrate, cool to room temperature, add alcohol to the concentrated filtrate until the alcohol's concentration reaches 50%-70% by weight, allow it to stand and then separate the supernatant fluid; retrieve the alcohol of the supernatant fluid to form a liquid extract for further use; and E. mix the liquid extracts prepared in step A, step C and step D, condense the mixture further, carry out a drying procedure under vacuum condition; pulverize the resultant dry extract to form a fine powder; add proper excipients to the fine powder to make granules; mix the granules with the inclusion compound prepared in step B; and prepare the mixture into a clinically acceptable dosage form.

12. The method of claim 11 wherein the dosage form is at least one selected from the group consisting of tablet, capsule and granules.

13. A method for preparing a pharmaceutical composition comprising the steps as follows:

I. providing the herbs:

| | | |
|---|---|---|
| Prepared fleece flower root | 400 g dodder | 200 g |
| pseudostellaria root | 600 g prepared atractylodes rhizome | 120 g |
| wolfberry fruit | 400 g achyranthes root | 400 g |
| lycopus herb | 400 g red peony root | 400 g |
| Poria | 600 g alisma rhizome | 400 g |
| Asiatic plantain seed | 600 g prepared rhubarb | 240 g |

II. preparing steps as follows:

A. prepared fleece flower root and prepared rhubarb are crushed into coarse powder and soaked in 70% alcohol for 24 hours, and then percolated at the speed of 2 mL/min to obtain about 5.12 liter solution; alcohol in this solution is removed; and then the dealcoholized solution is condensed to obtain the fluid extract;

B. prepared atractylodes rhizome is crushed into coarse powder and soaked in water 5 times the weight of the herb for 4 hours; then the soaked atractylodes rhizome powder is distilled with vapor to obtain the volatile oil; the remaining portion after the distillation is reserved for further use; the volatile oil is dissolved by routine quantum of alcohol, then ground with β-cyclodextrin and water together by colloid mill, wherein the ratio of volatile oil to β-cyclodextrin is 1:8, the ratio of β-cyclodextrin to water is 1:2, the distance between the 2 mill surfaces is 5 μm, and the milling speed is 3,000 rpm; after 15 minutes of grinding, a paste is obtained; then the paste is dehydrated and crushed into powder to obtain the clathrate of the volatile oil;

C. the wolfberry fruit and poria are cooked in the water 3 times to obtain the liquor and each time is for a duration of 2 hours, the weight of the water is 8 times the weight of the two herbs; the liquors are collected and condensed to the relative density 1.1 at the temperature of 80° C.; then the condensed liquor is concentrated to get a centrifugate;

D. the remaining portion of atractylodes rhizome after distillation in step B is mixed with the remaining 7 kinds of herbs: pseudostellaria root, lycopus herb, psyllium seed, dodder, achyranthes root, red peony root and alisma rhizome, together and cooked in the water 8 times by weight, for 2 times to obtain 2 cooked solutions; each time is 2 hours; the 2 cooked solutions are mixed, filtrated and condensed to obtain a paste with the relative density of 1.15 at the temperature of 80° C., and then the paste is cooled to room temperature; the cooled paste is added with alcohol until the alcohol's concentration reaches 65%, and then is left standing for 24 hours to obtain a supernatant fluid;

E. after the alcohol in the supernatant fluid is removed, the non-alcoholic supernatant fluid is mixed with the fluid extract prepared in step A from prepared rhubarb and prepared fleece-flower root, and the centrifugate prepared in step C from wolfberry fruit and poria to obtain a new mixture; this mixture is concentrated to a thick paste with the relative density 1.3 at the temperature of 80° C.; then the thick paste is dehydrated at the low pressure of −0.09 MPa and the temperature of 80° C., and then the dehydrated paste is crushed to fine powder; the fine powder is mixed with excipient to make a granule; the granule is mixed with the volatile oil β-cyclodextrin clathrate and pressed to 1,000 tablets; each tablet contains the effective ingredients equal to that contained in 4.76 g of the combination of herbs in Step I above; then the tablets are capsuled with a filmy coat to obtain the final product.

14. A method for treating chronic renal failure (CRF) comprising administering to a patient in need thereof a pharmaceutical composition for treating CRF, which comprises the herbs based on weight prorortion as follows:

| | |
|---|---|
| fleece-flower root | 100-600 parts by weight |
| cuscuta seed | 100-600 parts by weight |
| pseudostellaria root | 100-600 parts by weight |
| atractylodes rhizome | 100-600 parts by weight |
| wolfberry fruit | 100-600 parts by weight |
| achyranthes root | 100-600 parts by weight. |

* * * * *